United States Patent [19]

Hammer

[11] 4,009,714
[45] Mar. 1, 1977

[54] INTRAVENOUS SOLUTION FILTER UNIT

[75] Inventor: Kurt Finn Hammer, Camarillo, Calif.

[73] Assignees: Johnson & Johnson, New Brunswick, N.J.; Purolator, Inc.,, Del.

[22] Filed: July 30, 1975

[21] Appl. No.: 600,673

[52] U.S. Cl. .................... 128/214 R; 128/214 C; 210/445
[51] Int. Cl.² ................................... A61M 5/16
[58] Field of Search ....... 128/214 R, 214 C, 214 Z; 210/247, 306, 310, 436, 445, 456, DIG. 23; 55/159

[56] References Cited
UNITED STATES PATENTS

| | | |
|---|---|---|
| 2,530,283 | 11/1950 | Brown ........................... 210/445 |
| 3,034,504 | 5/1962 | Winsor et al. ................. 128/214 Z |
| 3,506,130 | 4/1970 | Shaye ............................ 210/436 |
| 3,803,810 | 4/1974 | Rosenberg ....................... 55/159 |
| 3,905,905 | 9/1975 | O'Leary et al. ................ 210/436 |

*Primary Examiner*—Dalton L. Truluck

[57] ABSTRACT

A self-priming filter unit for filtering intravenous solutions. The filter unit is substantially rectangular in shape with an inlet at the bottom portion of the filter. The inner surface of the housing on the downstream side of the filter medium is grooved so as to cause air to flow to the outlet as the filter unit is being filled with liquid.

5 Claims, 8 Drawing Figures

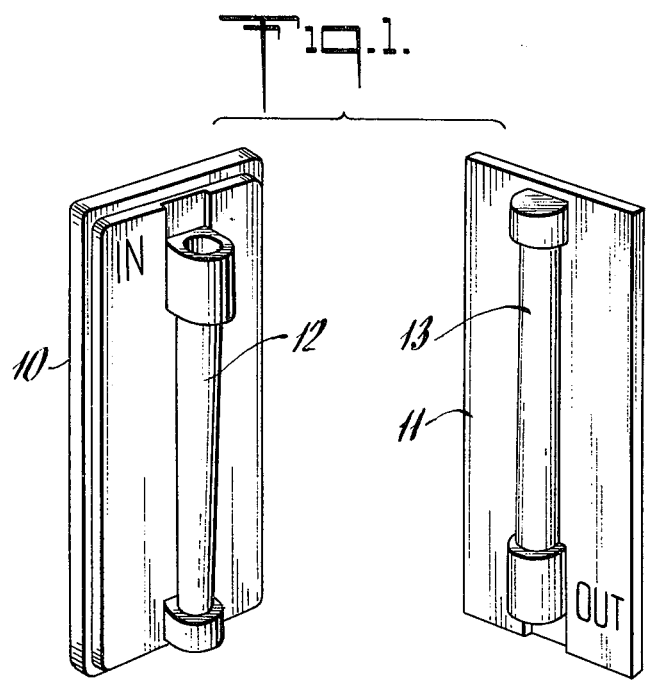
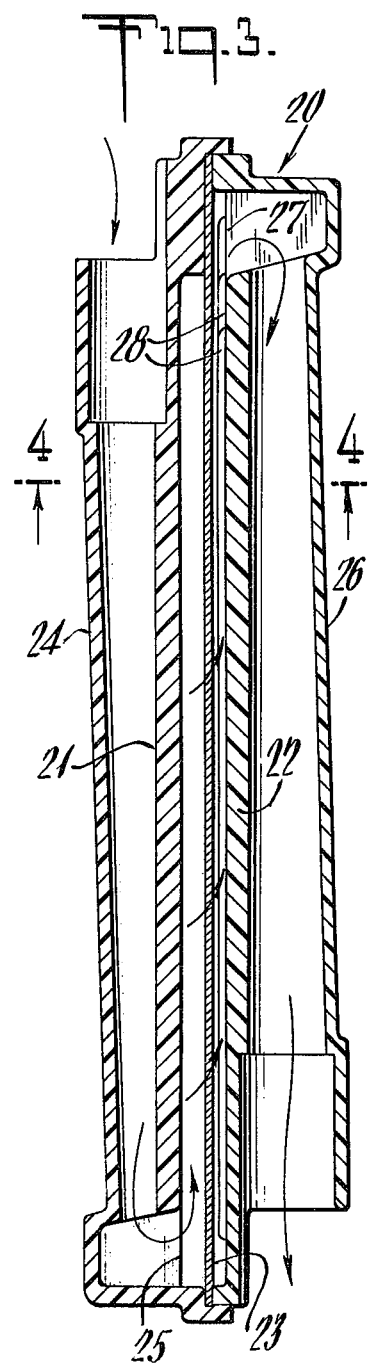
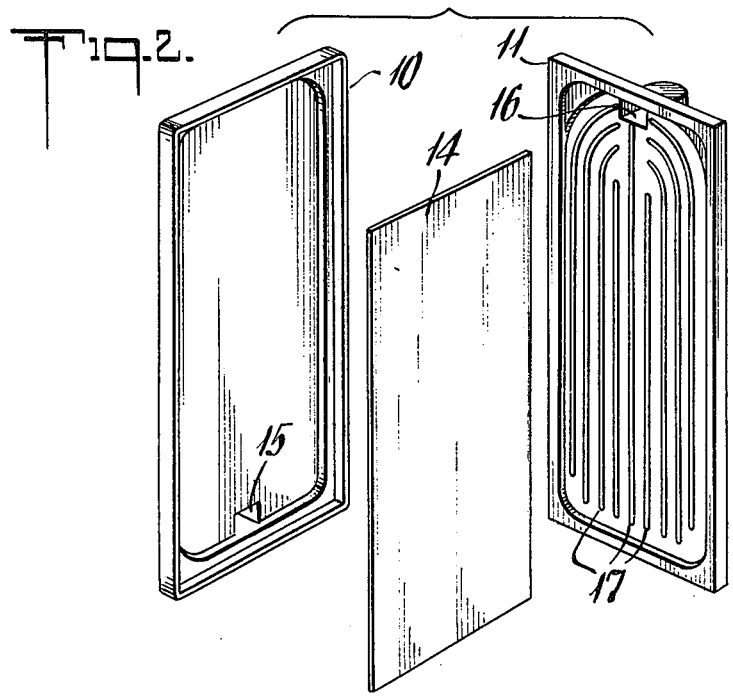
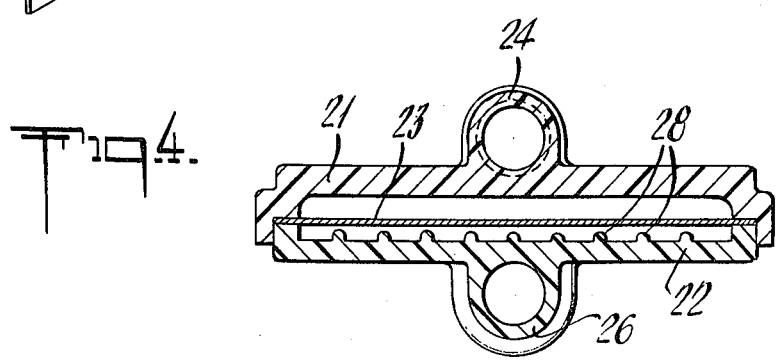

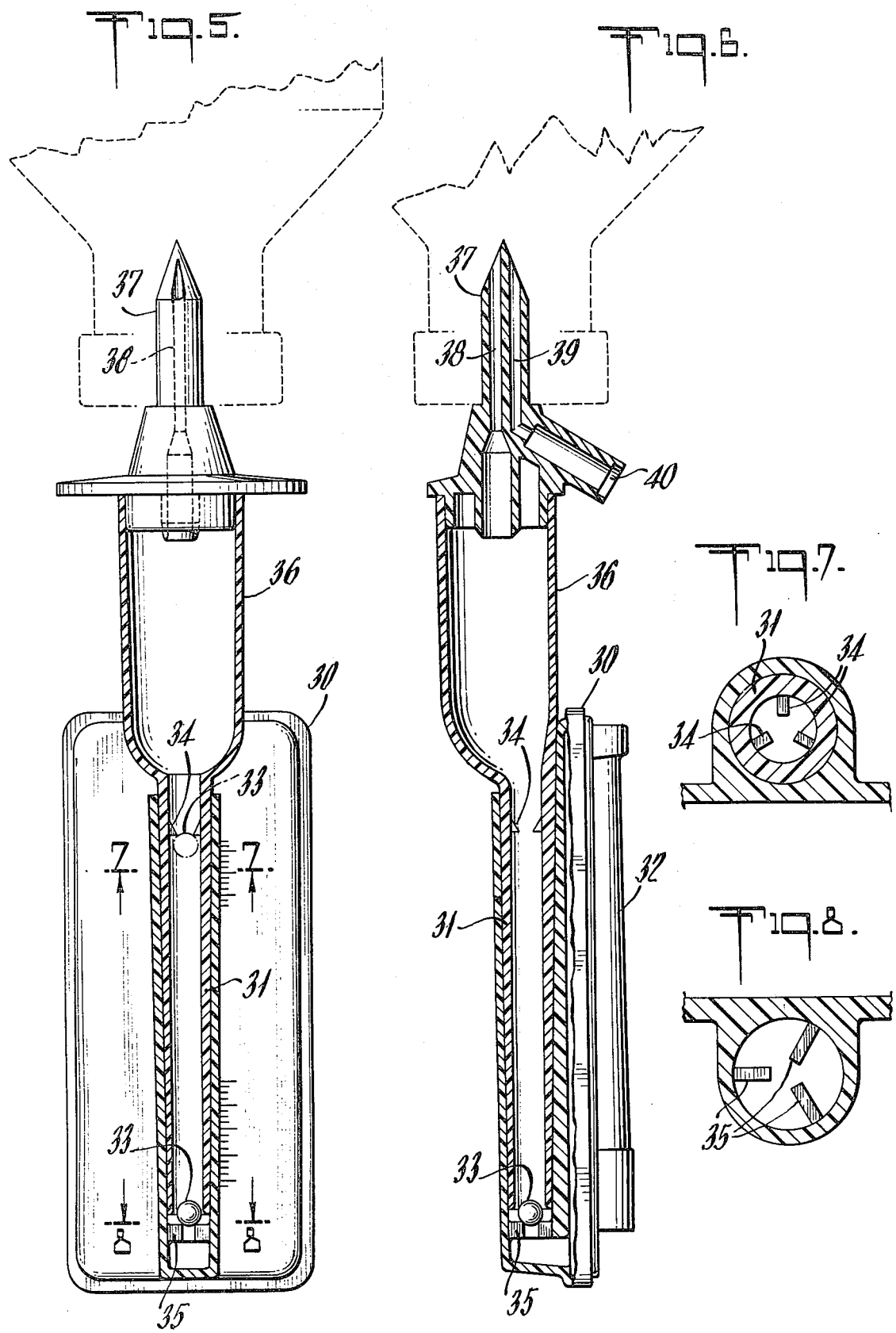

INTRAVENOUS SOLUTION FILTER UNIT

The present invention relates to microporous filtering units for filtering intravenous solutions.

BACKGROUND OF THE INVENTION

In the administration of intravenous solutions to patients, it is desirable that the solutions be filtered to prevent the administration of particulate matter of harmful bacterial organisms to the patient. The possibility of particulate matter being present in the solution has increased over the past years with the increasing use of additives to the IV solution. The possible infusion of particulate matter into the vein of a patient is undesirable and in recent years a number of final filters have been developed which are used in the administration line of the intravenous solution. Generally, these filters use a filter media having a pore size rating of anywhere from about 0.22 microns to 10 microns. Usually the filter media has a pore size rating of about 0.45 to 5 microns. Membranes of 0.45 microns do an acceptable job and can be used for sterile filtration, however, in some instances there are organisms smaller than 0.45 microns present in the IV solution. In these instances a 0.22 micron filter might be used to give absolute sterilization. However, the problem with a 0.22 micron filter is that usually a pump is required in order to obtain the desired flow rates through the filter. When pumps are used to administer IV solutions, the cost to the patient is increased.

Fine filters used in the administration of IV solutions incorporate microporous filter media of 0.2 microns, 0.45 microns or even 1 micron or more are made from hydrophillic material in order to allow liquid to pass through the filter media. Such fine filter media will not pass air or gas once the media is wetted. This characteristic is desirable in that it prevents air or gas from being inadvertently transmitted to the patient. However, this characteristic requires that the filter be inverted and primed or vented before the solution is to be administered in order to insure that the air is removed before the entire filter media is wetted. In instances where air is not completely removed from the inlet side by priming or venting, entrapped air can block off a portion of the filter media and reduce the effective area of filtration and the effective life of the filter.

A number of elaborate purges or bypasses around the filter media have been developed to prevent this air blockage. Examples of these bypass or purging type filters are given in U.S. Pat. No. 3,677,242. In some instances a filter having a hydrophillic section and a hydrophobic section may be used. The hydrophillic section will pass the liquid to the patient and the hydrophobic section will pass the gas and is vented to the atmosphere. Such filters are expensive and costly to produce in that two different types of filter media have to be handled and sealed in the housing and these extra costs are passed on to the patient. An example of the combination hydrophillic-hydrophobic filters is given in U.S. Pat. No. 3,803,810.

SUMMARY OF THE PRESENT INVENTION

We have discovered an improved microporous intravenous filter unit. Our improved filter unit uses media having a mean pore size rating of approximately 0.2 microns and our new unit can be used for absolute bacterial sterilization. Our new unit does not require a pump and with standard gravity flow has a sufficient flow rate and total capacity for the administration of at least 4 liters of most intravenous solutions to patients. Hence, our new improved filter unit is economical to produce and economical in cost to the patient. Our improved filter unit is self-priming in that the air automatically escapes from the unit as it is being filled eliminating complicated manipulations required of the nurse or the physician who is administering the intravenous solution. The self-priming feature does not require the addition of hydrophobic-type filter media and allows for simplified construction of our filter unit which again reduces its cost and the ultimate cost to the patient.

In accordance with the present invention, our new self-priming filter unit for filtering intravenous solution comprise a substantially rectangular housing. A0.2 micron microporous filter medium substantially the same shape and coextensive with the housing is disposed in the housing and sealed about its periphery to the housing. On the upstream side of the medium and disposed at the bottom lower portion on the short side of the housing is an inlet. On the downstream side of the medium and disposed at the upper or opposite portion of the housing on the short side thereof is an outlet. The inner surface of the housing on the downstream side of the filter medium contains a plurality of ridges which extend from the side opposite the outlet to the outlet to guide the flow of air as the filter is being primed from the bottom of the unit to the outlet and provides a support for the filter medium against the differential pressure head.

Various embodiments of our new filter unit may include a drip chamber disposed immediately before the inlet or immediately after the outlet. Other embodiments of our new filter may also incorporate a flow indicator, an air vent, and in some instances, a hand pump or various combinations as desired.

BRIEF DESCRIPTION OF THE DRAWINGS

The invention will be more fully described in conjunction with the accompanying drawings wherein:

FIG. 1 is an exploded perspective view of the outside surfaces of a filter unit in accordance with the present invention. The two halves of the filter housing have been rotated about 270° with respect to each other to provide this view.

FIG. 2 is an exploded view of a filter unit according to the present invention. The two halves of the housing are rotated about 90° with respect to each other with the filter medium disposed between the two halves to provide this view.

FIG. 3 is an enlarged cross-sectional view of a filter unit according to the present invention.

FIG. 4 is a cross-sectional view taken along line 4—4 of FIG. 3.

FIG. 5 is a partial, cut-away plan view of another embodiment of the new filter unit of the present invention.

FIG. 6 is a partial, cut-away view of the filter unit of FIG. 5 taken at 90° to the view shown in FIG. 5.

FIG. 7 is a cross-sectional view taken along line 7—7 of FIG. 5.

FIG. 8 is a cross-sectional view taken along line 8—8 of FIG. 5.

DETAILED DESCRIPTION OF THE DRAWINGS

Referring to the drawings in FIGS. 1 and 2, there is shown a new improved intravenous filter unit in accordance with the present invention. The unit comprises an upstream filter housing half 10 and a downstream filter housing half 11. In FIG. 1 the upstream half and the downstream half have been rotated 270° with respect to each other so that you see the two outer surfaces of our new filter. On the outside surface of the upstream housing half extending the length of the filter is an inlet conduit 12. On the outside surface of the downstream housing half extending the length of the filter is an outlet conduit 13. The conduits are designed to accept the standard tubing used to administer intravenous solutions.

In FIG. 2 the filter shown in FIG. 1 has been opened in the opposite direction with the upstream housing half 10 and downstream housing half 11 rotated at 90° with respect to each other and with the filter medium 14 disposed between the two halves. The halves are rectangular in shape and coextensive, preferably one of the halves fits snugly into the opposite half. Disposed between the two filter halves and coextensive therewith is the microporous filter medium 14. The medium is sealed about its periphery to the two halves of the filter and the halves of the filter sealed together to form an air and liquid tight filter unit. At the bottom and along the shorter edge of the upstream filter half of the housing is the inlet opening 15 for the solution to be filtered. This inlet opening cooperates with the inlet conduit 12 described in conjunction with FIG. 1. At the upper portion and along the shorter side of the downstream filter half of the housing is the outlet 16 for the solution that has been filtered. The outlet opening cooperates with the outlet conduit 13 described in conjunction with FIG. 1.

As shown in FIG. 2, the inner surface of the downstream half of the housing includes a series of ridges 17 which extend from the end opposite the outlet opening to the outlet opening in a converging manner.

In FIGS. 3 and 4 there are shown enlarged cross-sectional views of the new and improved filter of the present invention. The filter unit 20 comprises an upstream filter housing half 21 and a downstream filter housing half 22. The downstream half is slightly smaller than the upstream half and fits snugly into the upstream half as shown in FIG. 4. The filter medium 23 is positioned between the two housing halves and is sealed about its periphery to at least one of the housing halves and the housing halves sealed together about their periphery to produce an air tight seal. An inlet conduit 24 extends substantially the length of the filter and connects to the inlet opening 25 positioned at the bottom of the upstream filter half. An outlet conduit 26 extends substantially the length of the filter and connects to the outlet opening 27 positioned at the top of the downstream filter half. The inside surface of the downstream filter housing half contains a plurality of ridges 28. The ridges extend from the bottom of the filter to the top of the filter and converge towards the outlet opening.

In utilizing our new filter unit, it is preferably started in a vertical position. The unit should be positioned at least 20° from a horizontal plane in order to be self-priming. Tubing from the intravenous solution to be administered to the patient is inserted in the inlet conduit 24. Tubing from the filter to the needle for administration is inserted into the outlet conduit 26. The intravenous solution flows into the filter through the inlet opening 25 and rapidly fills the cavity on the upstream side of the medium and, as the liquid level rises, the air is expelled from the upstream cavity through the dry portion of the medium to the downstream cavity. Then, with the upstream cavity filled, the liquid flows through and runs down the downstream side of the medium which slowly fills the downstream cavity. As the downstream cavity fills with liquid, the air is expelled through the outlet until the entire filter is filled with the solution. The solution is allowed to continue through to the needle to remove all of the air in the system before administration to the patient.

It is generally preferred that the housing be transparent so that the function of the filter unit may be observed while it is in use. Suitable materials that may be used for making the housing are polyethylene, polypropylene, certain polyacrylate polymers and the vinyl chloride polymers. Other materials may also be used including metals as long as they are not detrimental to the fluids and are inert while in use and may be readily sterilized.

The filter medium used is microporous and has a mean pore size rating of approximately 0.2 microns for absolute sterilization. Examples of suitable media are copolymers of acrylonitrile and polyvinyl chloride, cellulose esters and other polymeric materials.

The filter medium is sealed to the housing and two halves of the housing sealed together by solvent sealing, hot melt sealing, ultrasonic sealing or any of the well-known techniques to produce a tight seal against both gases and liquids. By tight seal, it is meant a 0.2 micrometer or better seal.

In use, the ridges on the inner surface of the downstream housing half also serve to prevent the medium from blocking itself off. In some instances, when the upstream pressure is too great, the medium is forced against the housing surface and the unit becomes partially blocked. The ridges support the filter media in spaced areas and eliminate this blocking problem.

The filter is rectangular in shape for a number of reasons. The rectangular shape assists the self-priming characteristic with the inlet at the bottom and the outlet at the top of the filter. This shape also allows for very efficient use of the filter medium so that a 0.2 micron medium may be used and there is sufficient area of the medium available to provide the flow rates necessary for administration of intravenous solutions by gravity flow. The shape also allows for the inexpensive production of the filter unit. The medium and housing, being substantially of the same size and shape, the handling, positioning, combining, sealing, etc. of the unit may be easily and readily automated with a minimum of different operations.

In FIGS. 5 through 8 there is shown a modification of the new and improved filter unit of the present invention. The basic filter unit 30 is similar to that described in conjunction with FIGS 3 and 4. The base unit comprises two filter housing halves with the medium disposed between the two halves. The upstream half includes an inlet conduit 31 and the downstream half an outlet conduit 32. The inlet conduit is tapered as shown and contains a ball flow indicator 33. The inlet conduit is also graduated along the filter housing so that you can read the flow rate from the ball directly from the filter and determine the rate at which the intravenous solution is being administered.

As shown in FIGS. 7 and 8 there are stops 34 at the top of the inlet conduit and stops 35 at the bottom of the inlet conduit to contain the ball within the conduit and to prevent it from becoming wedged or stuck during use. Extending upwardly from the inlet conduit is an enlarged chamber 36. The chamber is used as a drip chamber. Solution coming from an intravenous solution bottle will drip into the chamber and the drops may be counted so that the nurse or physician administering the solution can readily determine the flow rate. If desired, the chamber may be made of flexible material so that it can be squeezed and air expelled from the chamber of the IV bottle which will permit changing the liquid level in the chamber as desired. Extending upwardly from the drip chamber, is a spike 37 for inserting the entire unit into an intravenous solution container. The spike contains a conduit 38 connecting the solution container to the chamber and a second conduit 39 connecting the solution container to the atmosphere. The second conduit includes a liquid impermeable filter media 40 which will pass filtered air into the intravenous solution container and equalize the air pressure within the pressure within the container to provide a continuous flow of solution into the drip chamber.

Although in FIGS. 5 and 6 a number of modifications are shown, it should be noted that only one or two or any number of the modifications may be used alone or in various combinations. For example, just the filter unit with the flow indicator or the filter unit with the drip chamber incorporated and the like may be used.

Having fully described the invention it is intended that it shall be limited only by the scope of the claims appended hereto.

What is claimed is:

1. A self-priming filter unit for filtering intravenous solution comprising; a pair of rectangular housing members, each of said members having two parallel short sides and two parallel longer sides, a rectangular filter medium coextensive with said housing members and sealed at its periphery to the housing members, said housing members being sealed to each other at the periphery of said members, the upstream housing member having an inlet along the short side thereof at the bottom portion of the filter unit, said upstream housing member having an integral tubular conduit on the outside surface of said member extending from said inlet to the upper portion of said filter unit, the downstream housing member having an outlet along the short side thereof at the upper portion of the filter unit, the inner surface of said downstream housing member containing a plurality of ridges extending from the bottom portion of the filter unit to the outlet, and said downstream housing member having an integral tubular conduit on the outside surface thereof extending from said outlet to the bottom portion of the filter unit.

2. A self-priming filter unit according to claim 1 wherein the filter medium has a mean pore size of 0.2 microns.

3. A self-priming filter unit according to claim 1 wherein the integral tubular conduit on the upstream housing member is a flow indicator.

4. A self-priming filter unit according to claim 1 wherein the integral tubular conduit on the upstream housing member extends from a drip chamber.

5. A self-priming filter unit according to claim 1 wherein the integral tubular conduit on the upsteam housing member is a flow indicator and extends from a drip chamber.

* * * * *